US00PP30032P2

(12) United States Plant Patent
Delbard

(10) Patent No.: US PP30,032 P2
(45) Date of Patent: Dec. 25, 2018

(54) ***DAHLIA* PLANT NAMED 'SUNFIRE'**

(50) Latin Name: *Dahlia variabilis*
Varietal Denomination: Sunfire

(71) Applicant: Société Nouvelle Pépinières et Roseraies Georges Delbard SAS, Malicorne (FR)

(72) Inventor: Arnaud Delbard, Malicorne (FR)

(73) Assignee: Société Nouvelle Pépinières et Roseraies Georges Delbard SAS, Malicorne (FR)

( * ) Notice: Subject to any disclaimer, the term of this patent is extended or adjusted under 35 U.S.C. 154(b) by 0 days.

(21) Appl. No.: 15/732,115

(22) Filed: Sep. 20, 2017

(51) Int. Cl.
*A01H 5/02* (2018.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen M Redden
(74) *Attorney, Agent, or Firm* — Bethany Reid Roahrig; Cochran Freund & Young LLC

(57) ABSTRACT

A new cultivar of *Dahlia* plant named 'Sunfire' that is distinguishable by its naturally branched plant habit with multiple basal branches and lateral branches, dentate compound leaves, and large informal decorative type flowers which are bicolored yellow with bright red stripes and splashes, is disclosed.

2 Drawing Sheets

Genus and species: *Dahlia variabilis.*
Variety denomination: 'Sunfire'.

BACKGROUND OF THE NEW PLANT

The present invention relates to a new and distinct cultivar of *dahlia* grown for use in mixed combinations, beds and the landscape. The new variety is known botanically as *Dahlia variabilis* and will be referred to hereinafter by the cultivar name 'Sunfire'.

The genus *Dahlia* is in the family Compositae. The flower of 'Sunfire' is classified as an Informal Decorative *Dahlia*, consisting of twisty, curvy or wavy ray florets. The ray florets are arranged in whorls surrounding a central cluster of disc florets.

The inventor's *Dahlia* breeding program was commenced in 2007 in Commentry in central France. The objective of the breeding program is to combine certain desirable commercial characteristics of plant habit and flowers. The breeding programme is aimed at developing compact, naturally dwarf growth habits which do not require manual pinching or use of plant growth regulators, and large flowers with novel colors or color combinations including stripes and splashes.

The inventor's breeding stock consists of an isolated plot of *dahlia* varieties which have been selected or raised by the inventor from previous generations. The inventor allows open pollination of the breeding stock. Seed from the open pollinations is harvested and stored in October and November and sown in March of the following year, planted into the open ground in June and evaluated and, if very promising, set aside in August. Those selections which the inventor considers worthy of introduction are multiplied in the fall of the year of selection in the inventor's tissue culture laboratory. 'Sunfire' arose from the breeding program described above and was selected by the inventor in August 2009. The inventor selected 'Sunfire' for its large informal decorative flowers which are predominantly yellow in color and which exhibit bright orange-red stripes and splashes throughout the inflorescence.

The parents of 'Sunfire' are unknown and have not been released.

The first asexual reproduction of 'Sunfire' was conducted in fall 2010 using stem cuttings at the inventor's nursery in Commentry, France. Subsequent asexual propagation was carried out by stem cuttings and by in vitro cuttings in the inventor's laboratory. Under careful observation, the distinguishing characteristics have been determined stable, uniform, and to be reproduced true to type in subsequent generations of asexual propagation.

SUMMARY

The following traits have been repeatedly observed and represent the distinguishing characteristics of the new *Dahlia* cultivar named 'Sunfire'. These traits in combination distinguish 'Sunfire' from all other existing varieties of *Dahlia* known to the inventor. 'Sunfire' has not been tested under all possible conditions and phenotypic differences may be observed with variations in environmental, climatic, and cultural conditions, however, without any variance in genotype.

1. 'Sunfire' exhibits naturally branched plant habit with multiple basal branches and lateral branches.
2. 'Sunfire' bears compound trifoliate leaves with prominent dentate margins.
3. 'Sunfire' bears large informal decorative-type flowers whose ray florets twist and gently recurve.
4. The flowers of 'Sunfire' are bicolored consisting of yellow ground with bright red stripes and splashes.
5. 'Sunfire' is grown for use in mixed combinations, beds and the landscape.
6. 'Sunfire' blooms from summer until fall.

7. 'Sunfire' grows to 60 cm in height and width after one growing season
8. 'Sunfire' is hardy to USDA Zone 9.

DESCRIPTION OF THE PHOTOGRAPHS

The accompanying color photographs labeled FIG. 1 and FIG. 2 illustrate the overall appearance of the new *Dahlia* cultivar named 'Sunfire' showing the colors as true as is reasonably possible to obtain in colored reproductions of this type. Colors in the photographs may differ from the color values cited in the detailed botanical description, which accurately describes the actual colors of the new *Dahlia* variety named 'Sunfire'. The photographs were made from digital photographs of plants grown outdoors in Oxnard, Calif.

DESCRIPTION OF THE NEW VARIETY

Figure 1:
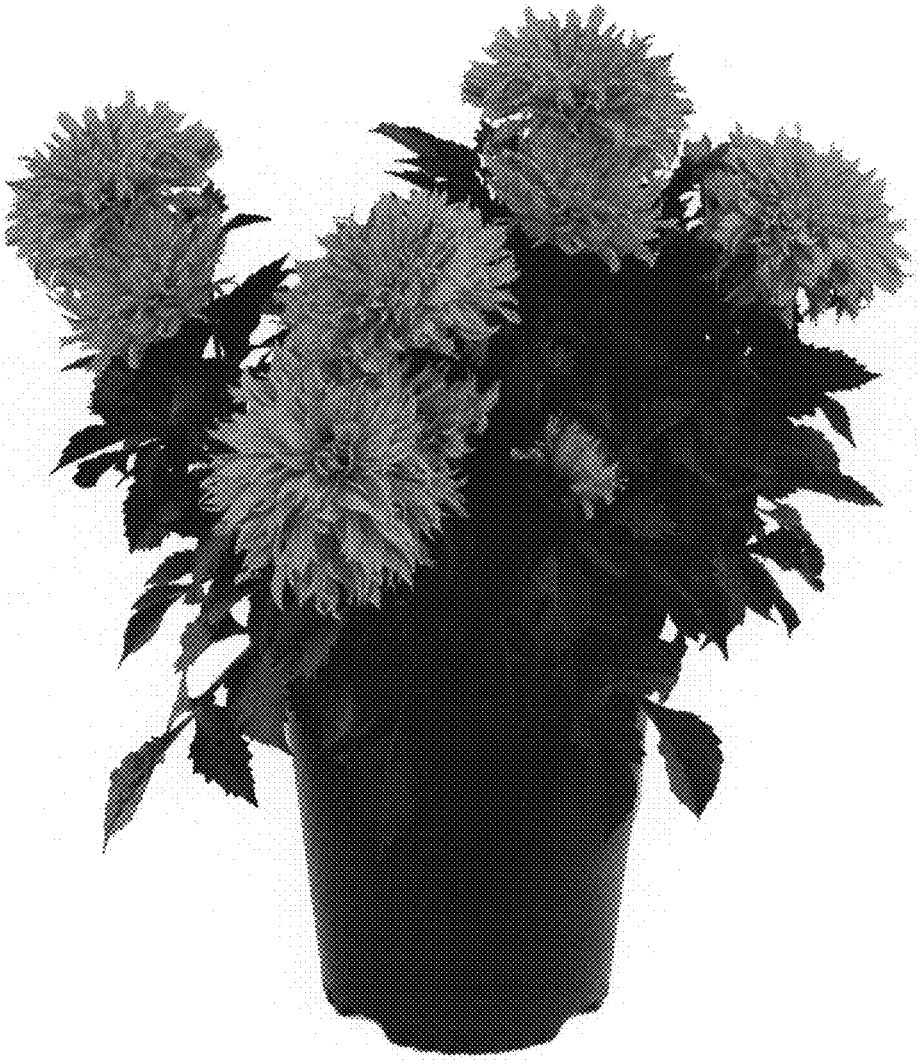
FIG. 1 depicts the entire plant in bloom showing the overall appearance of 'Sunfire' with typical bloom, foliage and habit.
Figure 2:
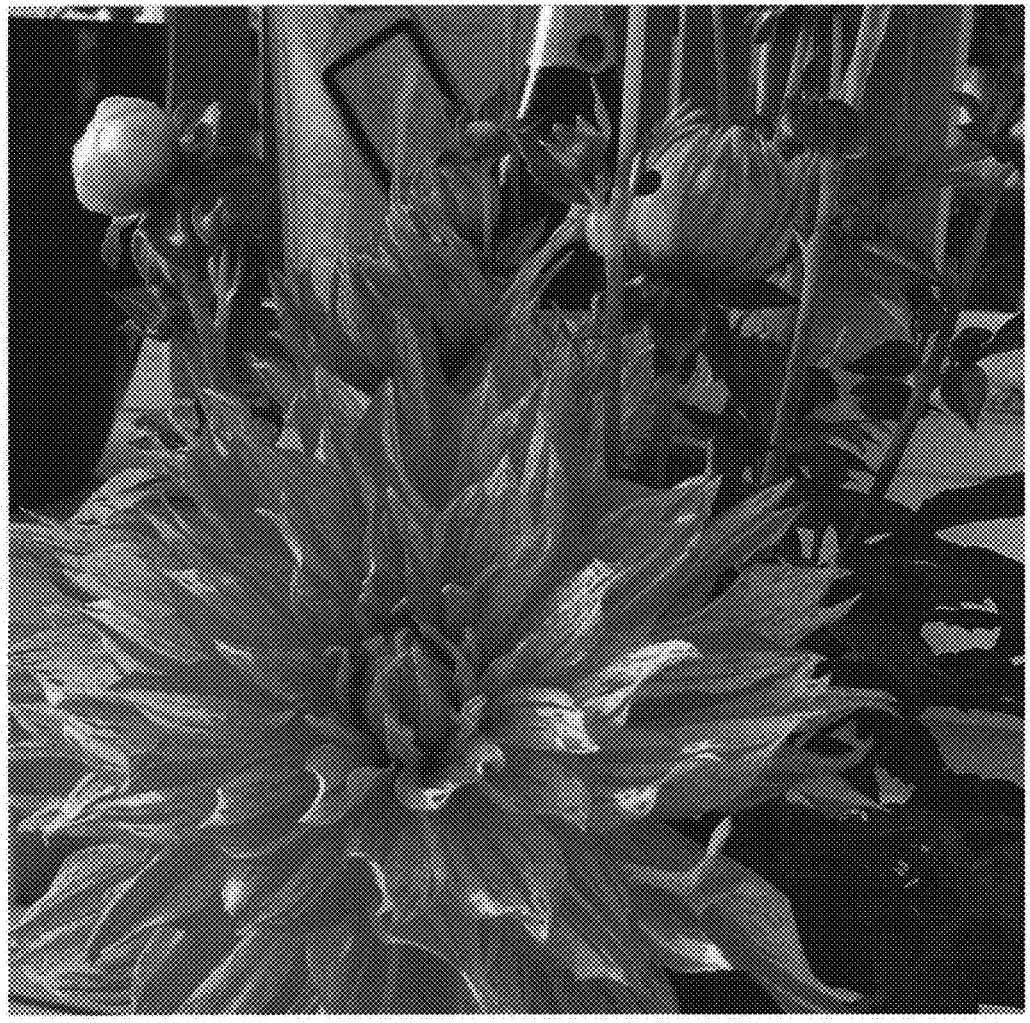
FIG. 2 depicts a close-up view of a flower of 'Sunfire'

The following is a detailed botanical description of the new *Dahlia* cultivar named 'Sunfire'. Observations, measurements, values and comparisons were collected during August 2017 in Santa Barbara, Calif. from 2-litre container plants. Color determinations were made in accordance with The 2007 Royal Horticultural Society Colour Chart from London England, except where general color terms of ordinary dictionary significance are used. Growing requirements are similar to the species. Growing requirements are similar to the species.

Botanical classification:

*Family*.—Compositae.
*Genus and species*.—*Dahlia variabilis*.
*Denomination*.—'Sunfire'.
*Common name*.—*Dahlia*.

Parentage: 'Sunfire' is a seedling selection made from plants grown from seed which resulted from the open-pollination of unknown and unreleased seedlings previously raised by the inventor.

Plant:

*Propagation method*.—Tissue culture, cuttings, tubers.
*Rooting system*.—Fine and fibrous.
*Tuber shape*.—Fusiform.
*Tuber size*.—10 cm average.
*Tuber color*.—165D.
*Vigor*.—Vigorous.
*Habit*.—Upright habit.
*Use*.—For use in mixed combinations, beds and the landscape.
*Type*.—Perennial in climate zones 9 and above; annual elsewhere.
*Dimensions*.—60 cm in height and width.
*Cultural requirements*.—Grow in full sun with regular water, and well-draining potting soil.
*Pest susceptibility*.—Susceptible to aphids.
*Disease susceptibility*.—Susceptible to mildew in highly humid conditions.

Stem and basal branches:

*Stem* (*below basal branches, unexposed*).—Length 3 cm, diameter 1 cm, shape cylindrical, surface coriaceous, color N199D.
*Basal branching habit*.—Naturally occurring (unpinched) basal branches with lateral branches.
*Basal branches*.—Number: 5 basal and lower stem branches. Dimensions: 30 cm in length and 8 mm to 10 mm in diameter at base. Shape: Cylindrical. Surface: Glabrous. Color: 148B. Internode length: 2.5 cm to 3.0 cm
*Lateral branches*.—Number: 0 to 5 lateral branches per basal branch. Dimensions: Up to 18 cm in length and 4 mm in diameter. Shape: Cylindrical. Surface: Glabrous. Internode length: 2.5 cm to 4.0 cm.

Foliage:

*Type*.—Compound, trifoliate.
*Leaflet shape*.—Lanceolate.
*Leaflet dimensions* (*terminal leaflet*).—Up to 10 cm in length, 8 cm in width.
*Leaflet dimensions* (*secondary leaflet pair*).—Up to 8.5 cm in length, 4.5 cm in width.
*Leaflet base*.—Acuminate.
*Leaflet apex*.—Acute, occasionally acuminate.
*Margin*.—Coarsely and irregularly dentate. Tooth shape acute or aristate. Tooth dimensions, height 3 mm, and width up to 10 mm. Number, 7 to 9 teeth per margin (14 to 18 teeth per leaflet).
*Color* (*adaxial surface*).—137B.
*Color* (*abaxial surface*).—138C.
*Venation pattern*.—Pinnate.
*Vein color* (*adaxial surfaces*).—138B.
*Vein color* (*abaxial surface*).—137C.
*Leaf surfaces* (*both surfaces*).—Glabrous.
*Compound leaf attachment*.—Petiolate.
*Leaflet attachment*.—Petiolate.
*Petiole shape*.—Sulcate.
*Petiole dimensions*.—Primary petiole (stem to secondary leaflet pair): 6 cm in length and 6 mm in width at stem. Petiole of secondary leaflets: 5 cm in length, 3.5 mm to 5.0 mm in width. Petiole of terminal leaflet: 2.5 cm to 3.5 cm in length, 2.5 mm to 3.0 mm in width.
*Petiole color*.—Adaxial surface: 152A with streaks 175C on older primary petioles; abaxial surfaces: 138C.
*Petiole surfaces*.—Glabrous.

Inflorescence:

*Inflorescence type and shape*.—Informal decorative type whose ray flowers (appearing as petals) are twisted along their length and gently recurved at their apex.
*Arrangement*.—The ray flowers are arranged in whorls surrounding a central cluster of disc florets.
*Aspect*.—Facing upward and outward.
*Inflorescence quantity*.—35 to 40 buds and flowers per 2-litre container plant.
*Dimensions of inflorescence*.—13 cm to 15 cm in diameter and 5 cm to 6 cm in height.
*Blooming season*.—Summer and fall.
*Lastingness of inflorescence*.—4 to 5 days.
*Self-cleaning or persistent*.—Self-cleaning.
*Fragrance of inflorescence*.—None observed.
*Peduncle*.—Dimensions (average): up to 8 cm in length and 3 mm to 5 mm in diameter. Shape: Cylindrical. Surface: Glabrous. Strength: Extremely stiff. Color: 145B below inflorescence, becoming 175C with age and towards peduncle base.
*Bud*.—Shape: Oblate. Dimensions (average): 13 mm in in diameter, 8 mm in height. Surface: Glabrous.

Appearance: Semi-glossy. Color: 143C at base becoming 151A towards and at apex. Apex: Obtuse. Base: Truncate.

*Ray florets*.—Quantity per inflorescence: Approximately 180. Arrangement: Whorls (8 to 10 per inflorescence). Form: Longitudinally twisted up to a quarter turn, apex recurved. Dimensions (when fully developed): 6 cm in length and 2.2 cm in width. Shape: Lanceolate. Surface (adaxial and abaxial): Glabrous. Apex: Acute, with single or double notch. Depth of notch up to 2 cm. Base: Attenuate. Margin: Entire. Color overall: A fully open inflorescence with all ray florets fully expanded appears bicolored yellow and red. The red coloration occurs in longitudinal stripes and splashes. Stripes run from base to apex and are up to 8 mm in width. Splashes are uniformly distributed and range between 1 mm and 5 mm in length and 0.25 mm and 0.5 mm in width. Color (adaxial surface): Bright yellow 9A with stripes and splashes bright red 42A. Color (abaxial surface): Cream-yellow 10A and soft red 45D. Corolla tube dimensions: 3 mm in length, 1.5 mm in diameter. Corolla tube color: 157D. Venation: Longitudinal parallel veins, depressed on adaxial surface, raised as ribs, typically three in number) on abaxial surface. Vein color (adaxial surface): 9A and 42A (as adjacent lamina). Vein color (abaxial surface): 10D.

*Disc florets*.—Disc diameter: 8 mm to 10 mm. Quantity of disc florets: 90 to 100 disc florets per inflorescence. Disc floret dimensions: 6 cm in length and 1 mm in width. Disc floret color: Ranges between N25A and N25C. Petals: 8 in number. Petals fused or unfused: Fused. Petal apex: Acute. Petal surface (both surfaces): Glabrous. Receptacle: Dome-shaped, 6 mm in depth and 12 mm in diameter. Receptacle surface: Glabrous. Receptacle color: 144A.

*Phyllaries*.—Arrangement: Densely packed whorl, consisting of approximately 20 concentric rings or layers. Number: Approximately 180 to 200. Shape: Lanceolate. Dimensions (largest, outermost): 22 mm in length, 9 mm in width, 1 mm in thickness at middle of phyllary base. Color: (adaxial and abaxial surfaces): Predominantly 1B except narrow elongated triangle 143C at base and extending to midpoint of phyllary. Surface texture: Waxy, glabrous. Appearance: Translucent. Apex: Rounded. Base: Truncate. Margin: Entire.

Reproductive organs (present of disc florets only):

*Stamens*.—5 in number, fused into tube around style.

*Stamen length*.—5 mm to 6 mm.

*Stamen color*.—10A.

*Anthers*.—Connate, tiny, less 0.5 mm in length and width.

*Anther color*.—N25C.

*Pollen*.—Sparse, none free.

*Pollen color*.—10B.

*Pistil*.—One in number.

*Pistil length*.—11 mm in length.

*Stigma form*.—Bifid, reflexed.

*Stigma dimensions*.—8 mm in length including 2 mm exserted.

*Stigma color*.—10A.

*Ovary position*.—Inferior.

*Ovary color*.—157D.

*Ovary shape*.—Obconical.

*Ovary dimensions*.—1 mm in width and 1.5 mm in height.

Seed: No seed observed to date.

COMPARISON TO COMMERCIAL VARIETIES

The varieties of *Dahlia* which are considered by the inventor to most closely resemble 'Sunfire' are *Dahlia* 'KLEDH17008' (unpatented) which is in commerce under the name Dalaya Yellow 18, and *Dahlia* 'KLEDH13037' (U.S. Plant Pat. No. 26,353) which is in commerce under the name Dalaya Devi. Whereas the flower colors of 'Sunfire' are yellow and bright red in color, the flowers of 'KLEDH17008' are yellow in color, and the flowers of 'KLEDH13037' are dark red in color. The plant height of both 'KLEDH17008' and 'KLEDH13037' ranges between 41 cm and 46 cm under the inventor's growing conditions, whereas the height of 'Sunfire' is 60 cm.

I claim:

1. A new and distinct cultivar of *Dahlia* plant named 'Sunfire' as described and illustrated herein.

* * * * *